US009061159B2

(12) United States Patent
Rahman

(10) Patent No.: US 9,061,159 B2
(45) Date of Patent: *Jun. 23, 2015

(54) USING THE CASE OF AN IMPLANTABLE MEDICAL DEVICE TO BROADEN COMMUNICATION BANDWIDTH

(71) Applicant: Boston Scientific Neuromodulation Corporation, Valencia, CA (US)

(72) Inventor: Md. Mizanur Rahman, Stevenson Ranch, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 223 days.

This patent is subject to a terminal disclaimer.

(21) Appl. No.: 13/875,089

(22) Filed: May 1, 2013

(65) Prior Publication Data

US 2013/0245720 A1 Sep. 19, 2013

Related U.S. Application Data

(63) Continuation of application No. 12/716,812, filed on Mar. 3, 2010, now Pat. No. 8,457,756, which is a continuation-in-part of application No. 12/616,178, filed on Nov. 11, 2009, now Pat. No. 8,577,474.

(51) Int. Cl.
*A61N 1/02* (2006.01)
*A61N 1/372* (2006.01)
*H01Q 1/22* (2006.01)
(Continued)

(52) U.S. Cl.
CPC ....... *A61N 1/37217* (2013.01); *Y10T 29/49018* (2013.01); *A61N 1/37229* (2013.01); *A61N 1/3758* (2013.01); *H01Q 1/22* (2013.01); *H01Q 1/44* (2013.01)

(58) Field of Classification Search
None
See application file for complete search history.

(56) References Cited

U.S. PATENT DOCUMENTS 4,561,443 A 12/1985 Hogrefe et al.
5,713,939 A 2/1998 Nedungadi et al.
(Continued)

FOREIGN PATENT DOCUMENTS

EP 1598092 11/2005
WO 2008/048724 4/2008
(Continued)

OTHER PUBLICATIONS

U.S. Appl. No. 11/215,946, filed Aug. 30, 2005, Yan et al.

*Primary Examiner* — Brian T Gedeon
(74) *Attorney, Agent, or Firm* — Lewis & Reese, PLLC

(57) ABSTRACT

An improved implantable pulse generator (IPG) containing improved telemetry circuitry is disclosed. The IPG includes a telemetry coil within the conductive IPG case, not in the non-conductive header as is typical, which simplifies IPG design. The improved resonant circuit of which the coil is a part does not include a discrete tuning resistor with the coil, which tuning resistor was traditionally used to increase communication bandwidth of the coil to render it suitable for FSK telemetry. In lieu of the tuning resistor, the coil is intentionally inductively coupled to the case by positioning the coil a certain distance away from the case. Such coupling decreases the effective inductance and increases the effective series resistance in the improved resonant circuit, both of which increase the communication bandwidth. As such, suitable FSK telemetry can be achieved, even though the improved resonant circuit without the case would not on its own have suitable bandwidth.

26 Claims, 6 Drawing Sheets

(51) Int. Cl.
    *H01Q 1/44* (2006.01)
    *A61N 1/375* (2006.01)

(56) References Cited

U.S. PATENT DOCUMENTS

| | | | |
|---|---|---|---|
| 5,735,887 A | 4/1998 | Barreras, Sr. et al. |
| 5,861,019 A | 1/1999 | Sun et al. |
| 6,009,350 A | 12/1999 | Renken |
| 6,516,227 B1 | 2/2003 | Meadows et al. |
| 6,553,263 B1 | 4/2003 | Meadows et al. |
| 6,701,188 B2 | 3/2004 | Stroebel et al. |
| 6,931,284 B2 | 8/2005 | Engmark et al. |
| 7,107,103 B2 | 9/2006 | Schulman et al. |
| 7,123,206 B2 | 10/2006 | Hess et al. |
| 7,177,698 B2 | 2/2007 | Klosterman et al. |
| 7,209,792 B1 | 4/2007 | Parramon et al. |
| 7,212,110 B1 | 5/2007 | Martin et al. |
| 7,379,775 B2 | 5/2008 | Parramon et al. |
| 7,428,438 B2 | 9/2008 | Parramon et al. |
| 7,554,493 B1 | 6/2009 | Rahman |
| 7,801,613 B2 | 9/2010 | Li et al. |
| 7,955,543 B2 | 6/2011 | Deininger et al. |
| 7,979,126 B2 | 7/2011 | Payne et al. |
| 8,010,205 B2 | 8/2011 | Rahman et al. |
| 8,081,925 B2 | 12/2011 | Parramon et al. |
| 8,170,680 B2 | 5/2012 | Ameri |
| 8,265,770 B2 | 9/2012 | Toy et al. |
| 2003/0171792 A1 | 9/2003 | Zarinetchi et al. |
| 2005/0149147 A1 | 7/2005 | Morgan et al. |
| 2008/0132974 A1 | 6/2008 | Strother et al. |
| 2009/0024179 A1 | 1/2009 | Dronov |
| 2009/0069869 A1 | 3/2009 | Stouffer et al. |
| 2010/0161002 A1 | 6/2010 | Aghassian |
| 2010/0211132 A1 | 8/2010 | Nimmagadda |
| 2011/0046699 A1 | 2/2011 | Mazanec |
| 2011/0112610 A1 | 5/2011 | Rahman et al. |

FOREIGN PATENT DOCUMENTS

| | | |
|---|---|---|
| WO | 2009/061537 | 5/2009 |
| WO | 2009/134466 | 11/2009 |

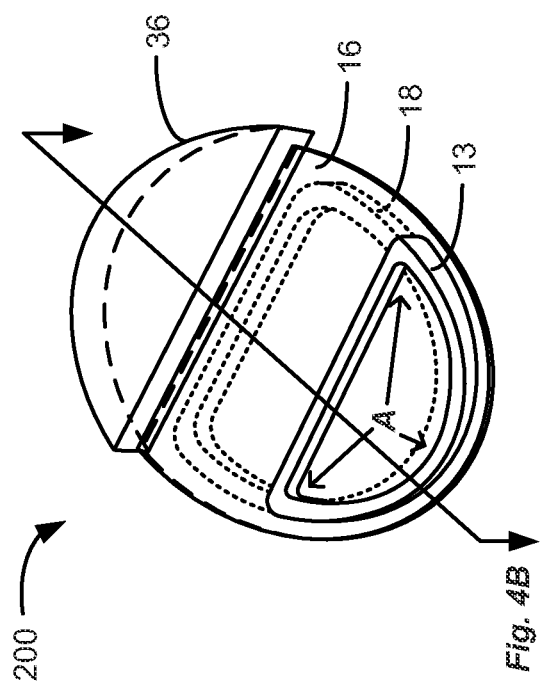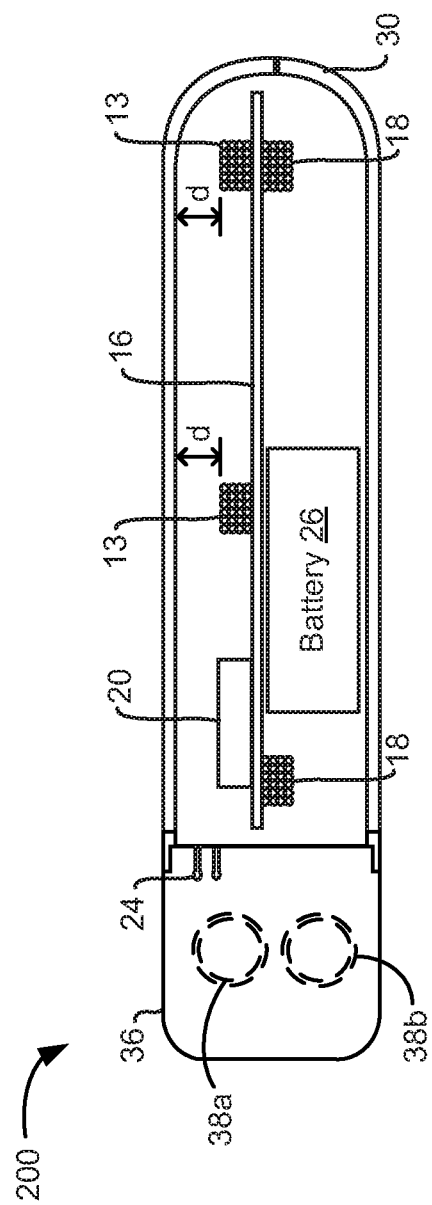

USING THE CASE OF AN IMPLANTABLE MEDICAL DEVICE TO BROADEN COMMUNICATION BANDWIDTH

CROSS-REFERENCE TO RELATED APPLICATIONS

This application is a continuation of U.S. patent application Ser. No. 12/716,812, filed Mar. 3, 2010, which is a continuation-in-part (CIP) of U.S. patent application Ser. No. 12/616,178, filed Nov. 11, 2009 ("the '178 application"). Priority is claimed to these applications, and both are hereby incorporated by reference in their entireties.

FIELD OF THE INVENTION

The present invention relates to an improved implantable medical device that utilizes coupling between a case and a telemetry coil instead of a discrete resistor to achieve suitable communication bandwidth.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

As shown in FIGS. 1A and 1B, a SCS system typically includes an Implantable Pulse Generator (IPG) 100, which includes a biocompatible device case 30 formed of a conductive material such as titanium for example. The case 30 typically holds the circuitry and battery 26 necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary. The leads 102, 104 couple to the IPG 100 using lead connectors 38a and 38b, which are fixed in a non-conductive header material 36, which can comprise an epoxy for example.

As shown in FIG. 2, the IPG 100 typically includes an electronic substrate assembly 14 including a printed circuit board (PCB) 16, along with various electronic components 20, such as microprocessors, integrated circuits, and capacitors mounted to the PCB 16. Two coils are generally present in the IPG 100: a telemetry coil 13 used to transmit/receive data to/from an external controller 12; and a charging coil 18 for charging or recharging the IPG's battery 26 using an external charger (not shown). The telemetry coil 13 is typically mounted within the header 36 of the IPG 100 as shown, and may be wrapped around a ferrite core 13'. Coil 13 is connected to the circuitry inside the case 30 via feedthrough connectors 24.

As just noted, an external controller 12, such as a hand-held programmer or a clinician's programmer, is used to wirelessly send data to and receive data from the IPG 100. For example, the external controller 12 can send programming data to the IPG 100 to dictate the therapy the IPG 100 will provide to the patient. Also, the external controller 12 can act as a receiver of data from the IPG 100, such as various data reporting on the IPG's status. The external controller 12, like the IPG 100, also contains a PCB 70 on which electronic components 72 are placed to control operation of the external controller 12. A user interface 74 similar to that used for a computer, cell phone, or other hand held electronic device, and including touchable buttons and a display for example, allows a patient or clinician to operate the external controller 12. The communication of data to and from the external controller 12 is enabled by a coil (antenna) 17.

Wireless data telemetry between the external controller 12 and the IPG 100 takes place via inductive coupling, and specifically magnetic inductive coupling. To implement such functionality, both the IPG 100 and the external controller 12 have coils 17 and 13 which act together as a pair. When data is to be sent from the external controller 12 to the IPG 100 for example, coil 17 is energized with an alternating current (AC). Such energizing of the coil 17 to transfer data can occur using a Frequency Shift Keying (FSK) protocol for example, in which digital data bits in a stream are represented by different frequencies. For example, frequency $f_0$ represents a logic '0' (e.g., 121 kHz) and frequency $f_1$ represents a logic '1' (e.g., 129 kHz). Energizing the coil 17 in accordance with these frequencies produces a magnetic field, which in turn causes coil 13 in the IPG to resonate. Such resonance induces a voltage in the IPG's coil 13, which produces a corresponding current signal when provided a closed loop path. This voltage and/or current signal can then be demodulated in the IPG 100 to recover the original data. Transmitting data from the IPG 100 to the external controller 12 occurs in essentially the same manner.

Typical communication circuitry for an IPG 100 such as that illustrated in FIGS. 1A, 1B and 2 is shown in FIG. 3A. An inductance $L_{coil}$ of the coil 13 and a capacitor C comprise a resonant circuit 75 that allows for both transmission and reception of FSK data signals. Although the inductance $L_{coil}$ and capacitance C are shown in series in resonant circuit 75, one skilled in the art will realize that such parameters can also be coupled in parallel. Generally, values for $L_{coil}$ and C are chosen so that resonance happens most strongly at a center frequency, $f_c$, which value is generally at the midpoint between $f_0$ and $f_1$ (e.g., 125 kHz). Coil 13 can be electrically modeled as having an inductance $L_{coil}$ and a self resistance, $R_{self}$. $R_{self}$ is the native resistance of the wire used to form the coil 13, and is measured at the AC operating frequency. Transceiver circuitry 54 and the microcontroller 55 are well known, and do not require substantial elaboration. One skilled will understand that the transceiver circuitry 54 includes amplifiers, modulators, demodulators, and other circuits to in effect translate a serial digital data stream to and from the IPG's process microprocessor 55, depending on whether data reception or transmission is occurring.

An important consideration in the design of the IPG's resonant circuit 75 is it bandwidth, because the bandwidth of the resonant circuitry needs to be wide enough to include both of the FSK frequencies $f_0$ and $f_1$. (The same is true for the matching resonant circuitry in the external controller 12, but because such circuitry is not the focus of this disclosure and can merely be the same as the circuitry in the IPG 100, such external circuitry is ignored). It is well known in the art, that the bandwidth of a series resonant circuit depends upon its quality factor (Q). The quality factor, Q, depends on the inductance, the resistance in series with the coil, and the center frequency:

$$Q = \frac{2\pi f_c \cdot L_{coil}}{R} \quad (1)$$

Further, the half-power or −3 dB bandwidth of the resonant circuit is dependent on Q:

$$BW = \frac{2\pi f_c}{Q} \quad (2)$$

When these two equations are combined, the bandwidth can be expressed as:

$$BW = \frac{R}{L_{coil}} \quad (3)$$

In prior art IPG resonant circuits 75, it was generally required to specifically add an additional discrete resistor, $R_{tune}$, to increase the bandwidth to a suitable level inclusive of $f_0$ and $f_1$. This is illustrated in FIG. 3B, which shows the frequency responses when $R_{tune}$ is included (curve 59) and not included (curve 58) in the resonant circuit 75. When $R_{tune}$ is not included in the circuit (curve 58), the bandwidth 63 (measured at −3 db line 60) does not include FSK frequencies $f_0$ or $f_1$, meaning that the communication would be inadequate to either transmit or receive such frequencies. By contrast, when $R_{tune}$ is included in the circuit (curve 59), the bandwidth 62 (measured at −3 db line 61) includes FSK frequencies $f_0$ or $f_1$, meaning that such frequencies can be transmitted or received with good efficiency. Table 1 shows typical values for an exemplary prior art resonant circuit designed to operate at $f_0$=121 kHz and $f_1$=129 kHz with a center frequency of $f_c$=125 kHz:

TABLE 1

| Parameter | Value |
| --- | --- |
| $L_{coil}$ | 1290 μH |
| $R_{self}$ | 26 Ω |
| $R_{tune}$ | 100 Ω |
| Q | 8 |
| Bandwidth | 15.5 kHz |

As can be seen, a tuning resistor $R_{tune}$ (100Ω) is needed which is significantly larger than $R_{self}$ (26Ω) to provide a suitable bandwidth (~15 kHz) to encompass $f_0$=121 kHz and $f_1$=129 kHz around the center frequency $f_c$=125 kHz with suitable margin. Without $R_{tune}$ included, the bandwidth decreases to about 3.1 kHz, which would range from about 123.5 to 126.5 kHz, and hence does not reach either of $f_0$ or $f_1$.

($R_{tune}$ can also be added in parallel to the $L_{coil}$ to broaden the bandwidth. However, because the value for $R_{tune}$ in this parallel configuration would usually be a lot higher than were $R_{tune}$ used in series with $L_{coil}$, a series connection is simpler).

The inventors consider certain aspects of the design of IPG 100 to be non-optimal. For one, the inventors find it unfortunate that the telemetry coil 13 resides in the IPG's header 36. This requires feedthroughs 24 (FIG. 2) to couple the coil 13 to the other resonant circuit 75 components and to the transceiver circuitry 54, all of which reside inside the case 30. Such feedthroughs 24 add to the complexity of the design of the IPG 100, and can lead to problems with hermeticity.

Another disadvantage of having the coil 13 in the header 36 is that the coil 13 takes up space in the header, which space is becoming more limited at IPG technology advances. It is desirable for patient comfort to continue to make IPGs 100 smaller, which shrinks header 36 volume accordingly. At the same time, future-generation IPGs are expected to offer even greater numbers of electrodes (e.g., 32, 64, etc). But accommodating an increased number of electrodes requires more space for lead connectors such as 38a and 38b (FIGS. 1A and 1B) in the header 36. As such, it is anticipated by the inventors that there may be little room left in the header for an adequate telemetry coil 13. Moreover, because the coil 13 in the header 36 must be rather small, a ferrite core 13' is usually beneficial to increase the magnetic flux through coil 13, and thus its communication efficiency. But the ferrite core 13' can potentially interfere with certain procedures, such as Magnetic Resonance Imaging (MRI), which limits the utility of designs using such cores.

It is also undesirable in the inventor's opinion to have to include a discrete tuning resistor $R_{tune}$ to tune the bandwidth of the communication circuitry. Current flowing through resistor $R_{tune}$ 53 dissipates heat in the specific location of that resistor, which "hot spot" can cause the resistor to either fail or deviate from its designed value, either of which adversely affects the reliability of the IPG 100. Moreover, it is generally desired to minimize the number of discrete components such as $R_{tune}$ in the case 30 of the IPG 100, because as just noted it is desirable to make the IPG 100 as small as possible and space inside the case 30 is limited.

A solution to these problems is provided in this disclosure in the form of a new mechanical and/or electrical design for an IPG, or other implantable medical device.

BRIEF DESCRIPTION OF THE DRAWINGS

FIGS. 4A and 4B show an improved IPG in accordance with the invention, in which the telemetry coil is within the IPG case and positioned a certain distance from the IPG case.

DETAILED DESCRIPTION

The description that follows relates to use of the invention within a spinal cord stimulation (SCS) system. However, it is to be understood that the invention is not so limited, and could be used with any type of implantable medical device system.

An improved implantable pulse generator (IPG) containing improved telemetry circuitry is disclosed. The IPG includes a telemetry coil within the conductive IPG case, not in the non-conductive header as is typical, which simplifies IPG design. The improved resonant circuit of which the coil is a part does not include a discrete tuning resistor in series or in parallel with the coil, which tuning resistor was traditionally used to increase communication bandwidth of the coil to render it suitable for FSK telemetry. In lieu of the tuning resistor, the coil is intentionally inductively coupled to the case by positioning the coil a certain distance away from the case. Such coupling decreases the effective inductance and increases the effective series resistance in the improved resonant circuit, both of which increase the communication bandwidth. As such, suitable FSK telemetry can be achieved, even though the improved resonant circuit without the case would not on its own have suitable bandwidth.

Figure 1:
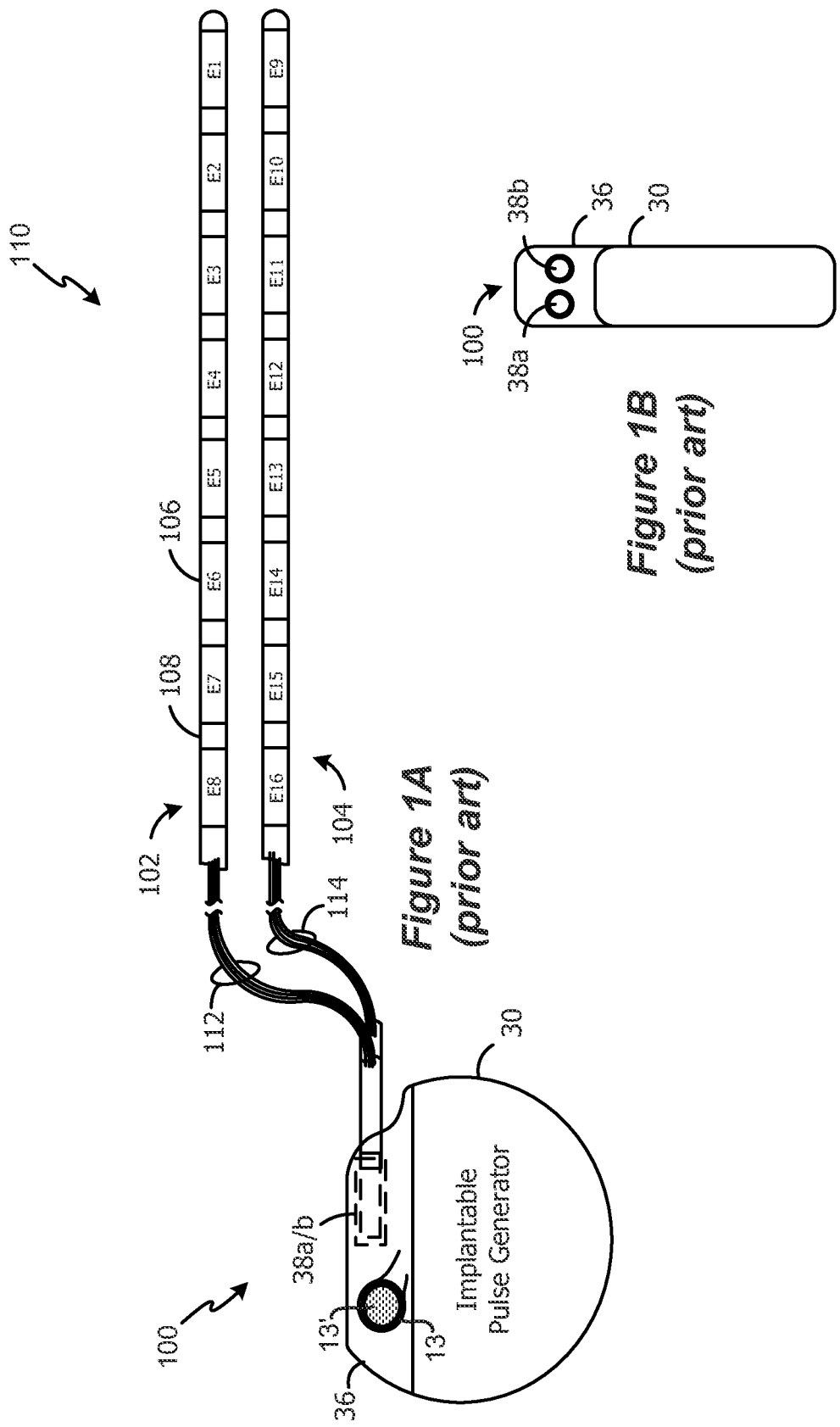
FIGS. 1A and 1B show an implantable medical device, and the manner in which an electrode array is coupled to the IPG in accordance with the prior art.
Figure 2:
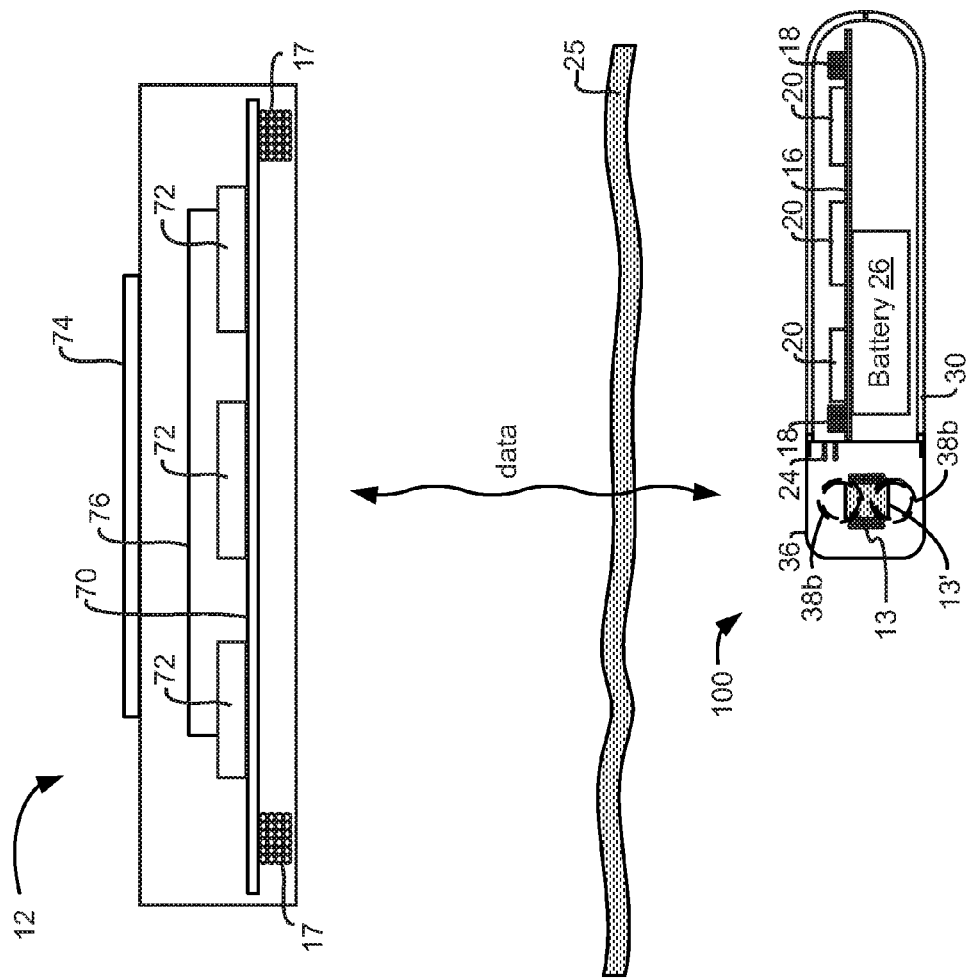
FIG. 2 shows the relation between the implantable medical device and an external controller.

An improved IPG 200 is shown in FIGS. 4A and 4B. Because the mechanical structure of IPG 200 is already discussed at length in the above-referenced '178 application, many of the details will not be reiterated here. In the design of IPG 200, the telemetry coil 13 is placed inside the case 30, and is wound in a plane parallel to a plane of the case. Because the telemetry coil 13 is placed inside the case 30, and not in the header 36 as in the prior art (FIG. 2), feedthrough connectors 24 (FIG. 2) are not required to couple the coil 13 to the remainder of the communication circuitry, which simplifies IPG design. Moreover, telemetry coil 13 is preferably made to encompass a large area A (FIG. 4A) when compared to the smaller coil 13 used in the header 36 in the prior art design. (The IPG's case 30 is removed in FIG. 4A for easier viewing). This larger area improves coupling, and hence reliability of data transfer, with the telemetry coil 17 in the external controller 12 (FIG. 2). Larger area A also compensates for the lack of a ferrite core 13' within the telemetry coil 13, which ferrite core is eliminated in the IPG 200. This again simplifies IPG design, and allows IPG 200 to be more compatible with Magnetic Resonance Imaging (MRI) techniques. Finally, by moving the telemetry coil 13 into the case 30, more room is left in the header 36 for the lead connectors, such as lead connectors 38a and 38b shown in FIG. 3B.

Figure 5:
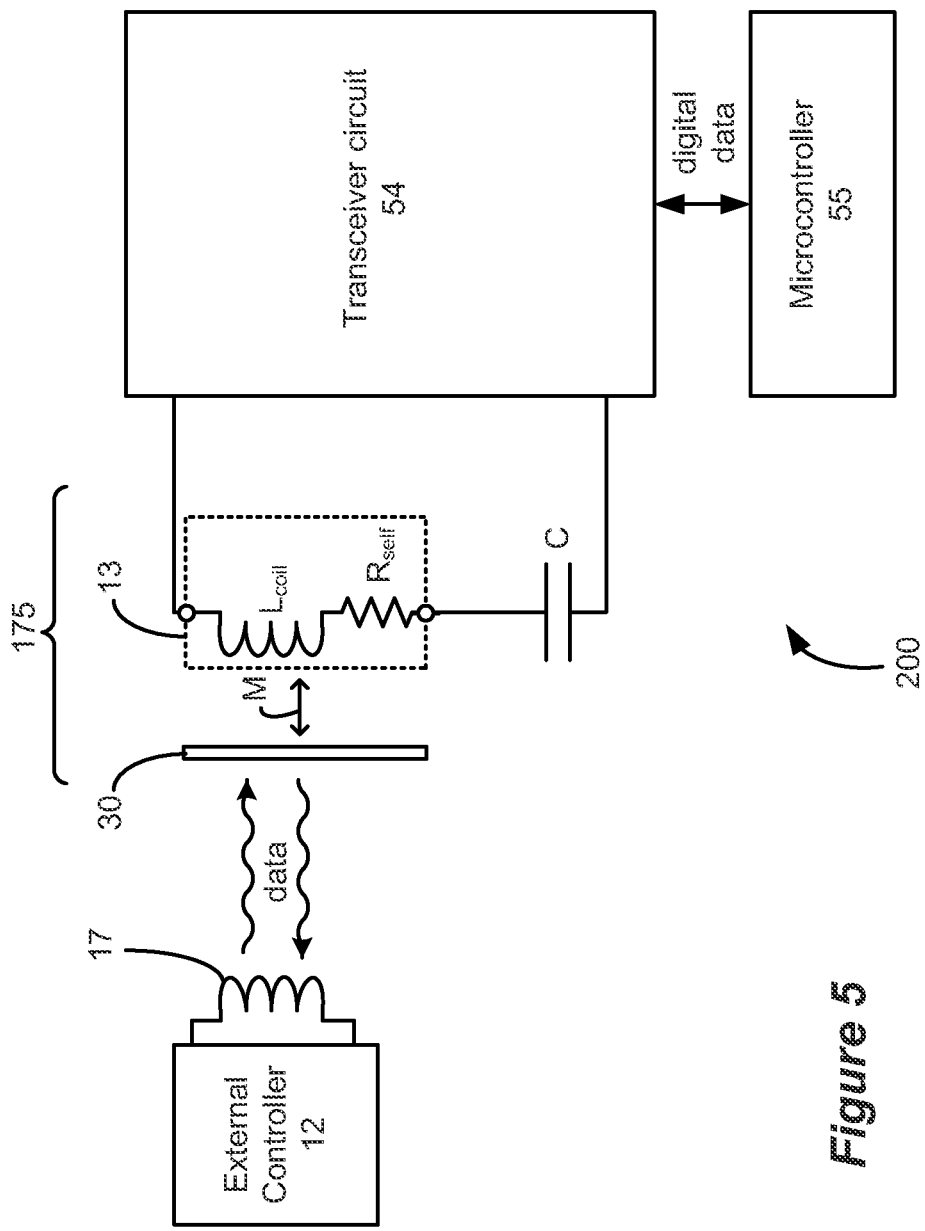
FIG. 5 shows the resonant circuit of the IPG of FIGS. 4A and 4B, and in particular shows that the tuning resistor of the prior art has been replaced by a coupling M between the coil and the case.

Changes to the mechanical design of the IPG 200 facilitate changes to the IPG 200's resonant circuit 175, which is shown in FIG. 5. As with resonant circuit 75, the improved resonant circuit 175 is shown with the tuning capacitance C in series with $L_{coil}$, although it could also be placed in parallel. Notice that unlike the prior art communication circuitry depicted in FIG. 3A, the improved resonant circuit 175 in FIG. 5 lacks a tuning resistor altogether. As such, the resonant circuit 175 is simpler, and omits a discrete resistor within the case 30 where space is at a premium. Additionally, concern over forming a "hot spot" at the location of such resistor is alleviated. Also present in FIG. 5 as part of the resonant circuit 175 is the IPG case 30, which is coupled to coil 13 by a coupling factor M. The relevance of the case 30 to the resonant circuit 175 will be explained shortly.

As noted earlier, in the prior art design, the tuning resistor, $R_{tune}$, was needed to adjust the bandwidth of the resonant circuit 75 to render it suitable for FSK telemetry: without the additional resistance of $R_{tune}$, the bandwidth was too narrow and would not encompass FSK frequencies $f_0$ and $f_1$. The improved resonant circuit 175 actually would suffer from this same bandwidth problem if treated in isolation. However, when the improved communication circuitry is properly positioned within conductive case 30, such coupling changes the parameters of the resonant circuit 175 to suitably broaden the bandwidth.

FIG. 4B shows the improved IPG 200 in cross section, and illustrates the positioning allowing for suitable FSK performance without the need for a discrete $R_{tune}$ resistor. Of specific importance is the distance, d, between the coil 13 and the conductive case 30. Traditionally in implant technology, it was generally desirable to isolate the coil 13 from the case 30 to the greatest extent possible to prevent interference or coupling between the coil 13 and the case 30, which interference could adversely affect the reliability of FSK data communications. However, in the improved design, distance d is intentionally made small to provide coupling to the case 30 and to broaden the communication bandwidth. This is counterintuitive, because as just mentioned coupling to the case can potentially degrade the reliability of data communication. However, such potential degradation is minimized in other ways, such as by providing a larger area extent A of the coil 13.

Because the case 30 is conductive, the AC magnetic fields generated by the telemetry coil 13—whether such coil is transmitting or receiving—cause eddy currents $I_e$ to flow through the conductive case 30 because of inductive coupling between the two. By Lenz's law, these circulating eddy currents will create induced magnetic fields in the case 30 that oppose the original magnetic field from coil 13. The induced eddy currents comprise power ($I_e^2 R_{case}$) loses within the case 30, where $R_{case}$ equals the resistance of the case. Such power loss will need to be compensated for by increasing the power draw in the transceiver circuitry 54.

Figure 6A:
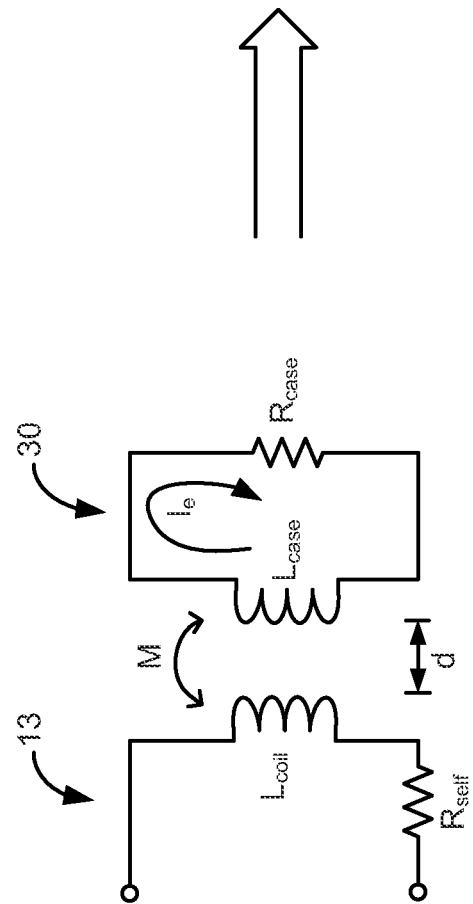
FIGS. 6A and 6B show equivalent circuits for the telemetry coil and the case when the telemetry coil is within the case at a distance d from the case.
Figure 6B:
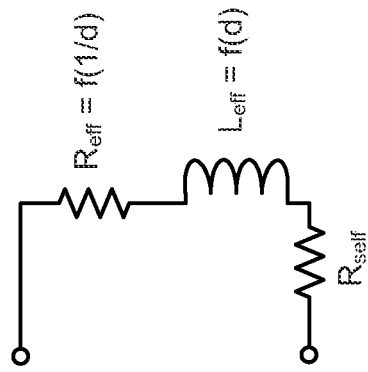

FIGS. 6A and 6B describe further the interaction between the telemetry coil 13 and the case 30. As shown in FIG. 6A, FIG. 6A shows the telemetry coil 13 and the conductive case 30. The telemetry coil 13 as before is represented by an inductance $L_{coil}$ and a resistance $R_{self}$. Case 30 is represented by an inductance $L_{case}$ and a resistance $R_{case}$. M represents the amount of coupling between the telemetry coil 13 and the case 30. d represents the distance between the telemetry coil 13 and the case 30, and is inversely related to the coupling factor, M.

An equivalent circuit for the network in FIG. 6A is shown in FIG. 6B. In the equivalent circuit, the inductive coupling between the case 30 and the coil 13 can be simplified as an resistance, $R_{eff}$ in series with an effective inductance, $L_{eff}$. ($R_{eff}$ generally scales with $R_{case}$). While one of ordinary skill in the art can represent $L_{eff}$ and $R_{eff}$ mathematically, it suffices here to observe that as the distance d decreases—i.e., as coil 13 is brought closer to the case 30—(1) $R_{eff}$ will increase, and (2) $L_{eff}$ will decrease from an initial value of $L_{coil}$ (i.e., $L_{eff} = L_{coil}$ at d=∞). (Such relations between distance d and $R_{eff}$ and $L_{eff}$ are more complicated than a simple linear or inverse linear relationship).

Returning to bandwidth Equation 3 discussed above, notice that that the increase in $R_{eff}$ and the decrease in $L_{eff}$ brought about by the coupling between the coil 13 and the case 30 both assist in increasing the bandwidth, BW. As such, when the bandwidth of the improved resonant circuit 175 is compared with (Eq. 4) and without (Eq. 5) the case, it can be seen that the former is larger (Eq. 6):

$$BW_{with\ case} = \frac{R_{self} + R_{eff}}{L_{eff}} \quad (4)$$

$$BW_{no\ case} = \frac{R_{self}}{L_{coil}} \quad (5)$$

$$BW_{with\ case} > BW_{no\ case} \quad (6)$$

Moreover, because the inclusion of the case 30 affects a larger change in series resistance resistance (i.e., from $R_{self}$ to $R_{self}$ $R_{eff}$) than it does a change in the inductance (i.e., from $L_{coil}$ to $L_{eff}$), $R_{eff}$ rather than $L_{eff}$ tends to dominate the increase in the bandwidth.

To further illustrate the increase in bandwidth that the case 30 provides in the improved resonant circuit 175, Table 2 represents exemplary values for the resonant circuit 175 with and without the case for a particular coil-to-case distance, d=2.5 mm, and assuming a resonant capacitor C of 5.4 nF:

TABLE 2

| Parameter | No Case | With Case |
|---|---|---|
| L | $L_{coil}$ = 325 µH | $L_{eff}$ = 300 µH |
| R | $R_{self}$ = 8 Ω | $R_{self}$ + $R_{eff}$ = 29 Ω |
| Q | 32 | 8 |
| BW | $BW_{no\ case}$ = 3.9 kHz | $BW_{with\ case}$ = 15.6 kHz |
| D | — | 2.5 mm |

Note as discussed above that the change from $R_{self}$ to $R_{self}$+ $R_{eff}$ (from 8 to 29Ω) is more pronounced than the change from $L_{coil}$ to $L_{eff}$ (from 325 to 300 µH), bearing out the dominance of $R_{eff}$ in effecting changes to the bandwidth.

Regarding such bandwidth changes, note from Table 2 that resonant circuit 175 without the case 30 would be ineffective for FSK communication at the frequencies noted earlier: at a bandwidth of 3.9 kHz, and assuming a center frequency $f_c$=125 kHz, such circuitry could only reliably resolve frequencies in the range of approximately 123 to 127 kHz, and so could not reliably transmit or receive communications at $f_0$=121 kHz or $f_1$=129 kHz. However, when the case 30 is included, the bandwidth increases to approximately 15.6 Hz, allowing resolution of frequencies from approximately 117 kHz to 133 kHz, which is able to resolve $f_0$ and $f_1$ with considerable margin. Although a bandwidth increase of four times (15.6/3.9) is experienced with these conditions, other useful embodiments of the technique can be defined as the case 30 contributing at least a two-times increase in bandwidth compared to the resonant circuit 175 in isolation.

Figure 3A:
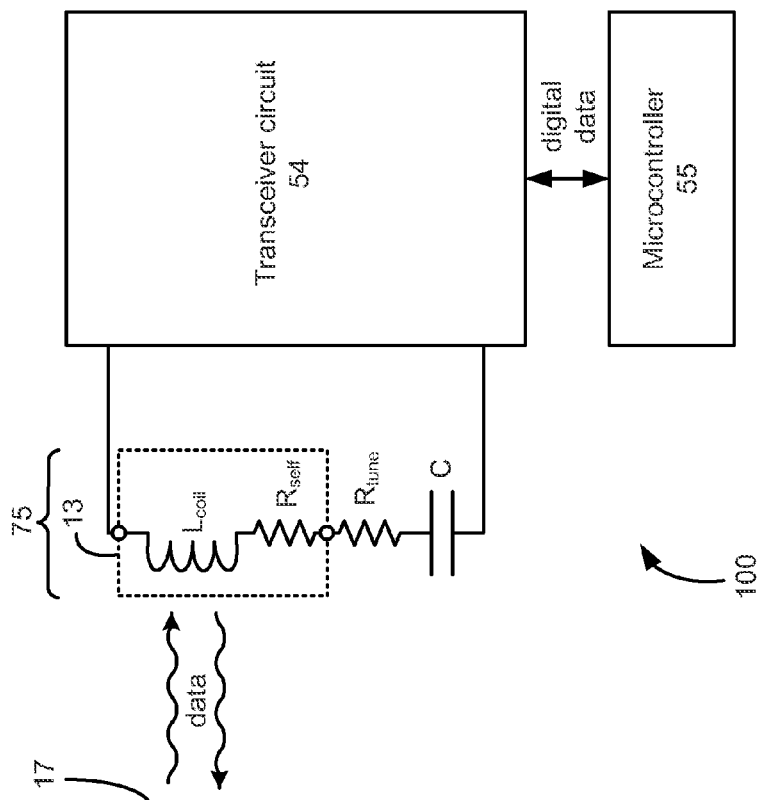
FIGS. 3A and 3B show the resonant circuit of the IPG of the preceding figures and in particular a tuning resistor and its effect on the bandwidth of the telemetry coil of the IPG.
Figure 3B:
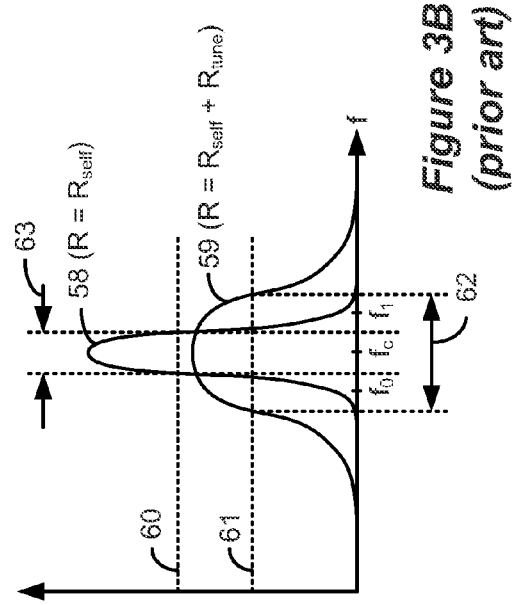

In short, the case 30 in the improve resonant circuit 175 replaces the function of $R_{tune}$ in the prior art resonant circuit 75 (FIG. 3A). Even if the increased effective series resistance $R_{eff}$ grows large and comprises a power draw, such power draw will not be limited to a discrete location, and instead will be distributed between the coil 13 and case 30, which beneficially spreads any heating in the IPG 100.

Proper tuning of the improve resonant circuit 175 requires the consideration of several factors, including at least $L_{coil}$, $R_{self}$, $R_{case}$, C, and distance d. It should be appreciated by one skilled in the art that computerized simulations may only be moderately helpful in choosing values for these different parameters given the complexity of the physics involved. For example, when choosing a particular distance d given fixed values for the other parameters in the resonant circuit 175, it may be advisable to build and test a prototype IPG, and to mechanically vary the distance d to see where d is optimized from a bandwidth and other perspectives. Such experimentation is fortunately routine for one skilled in the art, even if potentially time-consuming.

Although disclosed in the context of Frequency Shift Keying (FSK) using only two discrete frequencies to represent the two digital logic states of '1' and '0', it should be recognized that the disclosed technique for broadening the bandwidth is applicable to FSK techniques involving more than two discrete frequencies. As is known, $2^N$ frequencies can also be used to send $2^N$ digital symbols, with each symbol comprising N bits. For example, eight frequencies (e.g., 121, 122, 123, 124, 125, 126, 127, and 128 kHz) can be used to represent eight different digital symbols (e.g., 000, 001, 010, 011, 100, 101, 110, and 111), and the disclosed technique can be used to broaden the bandwidth to cover all eight frequencies. Such symbols can be considered as digital logic states for purposes of this disclosure.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device configured to transmit data to, receive data from, or transmit and receive data to and from, an external device with a first bandwidth, comprising:
   a planar conductive case;
   a resonant circuit within the conductive case comprising an antenna with an inductance and a resistance, wherein the antenna is located in a plane parallel to a plane of the conductive case, wherein the inductance and resistance of the antenna prescribe a second bandwidth for the resonant circuit;
   wherein the antenna is spaced at a distance to the conductive case to cause coupling between the antenna and the conductive case, whereby the coupling broadens the second bandwidth to a third bandwidth greater than the first bandwidth.

2. The device of claim 1, wherein the second bandwidth is smaller than the first bandwidth.

3. The device of claim 1, wherein the first, second, and third bandwidths comprise half-power bandwidths.

4. The device of claim 1, wherein the resistance comprises only a self-resistance of the antenna.

5. The device of claim 4, wherein the resonant circuit does not include a discrete resistor.

6. The device of claim 1, wherein the resonant circuit further comprises a capacitor.

7. The device of claim 1, wherein the capacitor is in series with the inductance.

8. The device of claim 1, wherein the capacitor is in parallel with the inductance.

9. The device of claim 1, wherein the antenna comprises a coil.

10. The device of claim 1, further comprising a non-conductive header coupled to the conductive case.

11. The device of claim 10, further comprising at least one lead connector within the non-conductive header for coupling to an electrode lead.

12. The device of claim 1, wherein the third bandwidth is at least double the second bandwidth.

13. The device of claim 1, further comprising a charging coil and a battery within the case, wherein the charging coil is configured to receive energy from an external charger to charge the battery.

14. The device of claim 1, further comprising a circuit board within the case, wherein the antenna is coupled to the circuit board.

15. The device of claim 1, wherein the data comprises data logic states or digital symbols at different frequencies within the first bandwidth.

16. A method for making an implantable medical device configured to transmit data to, receive data from, or transmit and receive data to and from, an external device with a first bandwidth, the method comprising:

provided a resonant circuit comprising an antenna with an inductance and a resistance, wherein the resonant circuit has a second bandwidth; and positioning the resonant circuit within a conductive case such that the antenna is spaced at a distance to the conductive case to cause coupling between the antenna and the conductive case, whereby the coupling broadens the second bandwidth of the resonant circuit to a third bandwidth greater than the first bandwidth.

17. The method of claim 16, wherein the second bandwidth is smaller than the first bandwidth.

18. The method of claim 16, wherein the first, second, and third bandwidths comprise half-power bandwidths.

19. The method of claim 16, wherein the resistance comprises only a self-resistance of the antenna.

20. The method of claim 19, wherein the resonant circuit does not include a discrete resistor.

21. The method of claim 16, wherein the resonant circuit further comprises a capacitor.

22. The method of claim 16, wherein the antenna comprises a coil.

23. The method of claim 16, further comprising a non-conductive header coupled to the conductive case.

24. The method of claim 23, further comprising at least one lead connector within the non-conductive header for coupling to an electrode lead.

25. The method of claim 16, wherein the third bandwidth is at least double the second bandwidth.

26. The method of claim 16, wherein the data comprises data logic states or digital symbols at different frequencies within the first bandwidth.

* * * * *